United States Patent
Ng et al.

(10) Patent No.: US 11,331,272 B2
(45) Date of Patent: May 17, 2022

(54) HYPERSTABILIZED LIPOSOMES INCREASE TARGETING OF MITOTIC CELLS

(71) Applicant: TEMASEK LIFE SCIENCES LABORATORY LIMITED, Singapore (SG)

(72) Inventors: Chang Zhi Adrian Ng, Singapore (SG); Shen-Yi Ian Cheong, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 16/478,278

(22) PCT Filed: Jan. 17, 2018

(86) PCT No.: PCT/SG2018/050026
§ 371 (c)(1),
(2) Date: Jul. 16, 2019

(87) PCT Pub. No.: WO2018/136002
PCT Pub. Date: Jul. 26, 2018

(65) Prior Publication Data
US 2019/0358161 A1 Nov. 28, 2019

Related U.S. Application Data

(60) Provisional application No. 62/447,498, filed on Jan. 18, 2017.

(51) Int. Cl.
*A61K 9/127* (2006.01)
*A61P 35/00* (2006.01)
(Continued)

(52) U.S. Cl.
CPC .......... *A61K 9/1271* (2013.01); *A61K 31/517* (2013.01); *A61K 31/519* (2013.01);
(Continued)

(58) Field of Classification Search
CPC .... A61K 9/127; A61K 9/1271; A61K 31/517; A61K 31/519; A61K 47/02; A61K 47/12; A61K 9/1278; A61P 35/00
See application file for complete search history.

(56) References Cited

U.S. PATENT DOCUMENTS

2009/0285881 A1* 11/2009 Dande .................. A61K 9/127
424/450
2011/0033461 A1* 2/2011 Ratushny ............. A61K 31/517
424/133.1

(Continued)

FOREIGN PATENT DOCUMENTS

| CN | 103948545 A | 7/2014 |
|---|---|---|
| EP | 2415470 A1 | 2/2012 |

(Continued)

OTHER PUBLICATIONS

Trosko, J.e., et al in Mutation Research, 480-481, pp. 219-229, 2001.*

(Continued)

*Primary Examiner* — Gollamudi S Kishore
(74) *Attorney, Agent, or Firm* — Rothwell, Figg, Ernst & Manbeck, P.C.

(57) ABSTRACT

Hyperstable liposome comprising an anti-mitotic agent, one or more anions and one or more cations entrapped in the inner milieu, wherein the entrapped anti-mitotic drug is released at a slow rate that is less than 0.6% in 12 hours or less than 5% in 8 hours when the liposomes are suspended in 600 mM sucrose. These liposomes are useful in the treatment of cancer. In particular, HEPC:Chol:DSPE-PEG2000 (50:45:5) liposomes comprising BI 2536 and citrate:phosphate in a ratio of 1:3.

20 Claims, 9 Drawing Sheets

(51) Int. Cl.
*A61K 31/517* (2006.01)
*A61K 31/519* (2006.01)
*A61K 47/02* (2006.01)
*A61K 47/12* (2006.01)

(52) U.S. Cl.
CPC .............. *A61K 47/02* (2013.01); *A61K 47/12* (2013.01); *A61P 35/00* (2018.01)

(56) References Cited

U.S. PATENT DOCUMENTS

| | | | |
|---|---|---|---|
| 2012/0171283 A1 | 7/2012 | Hong et al. | |
| 2012/0301537 A1* | 11/2012 | Ishida | A61K 31/513 424/450 |
| 2013/0115273 A1* | 5/2013 | Yang | A61K 9/1272 424/450 |
| 2013/0216609 A1* | 8/2013 | Lichter | A61K 31/496 424/450 |
| 2014/0220110 A1* | 8/2014 | Hayes | A61K 31/4196 424/450 |
| 2014/0271821 A1* | 9/2014 | McGhee | A61K 9/127 424/450 |
| 2016/0030340 A1* | 2/2016 | Kan | A61K 31/475 424/450 |
| 2016/0106672 A1* | 4/2016 | Hong | A61K 9/1278 424/450 |
| 2016/0113873 A1* | 4/2016 | Munson | A61K 9/0019 424/450 |
| 2016/0175250 A1* | 6/2016 | Downing | A61K 9/1277 424/450 |
| 2017/0035894 A1* | 2/2017 | Vlahov | C07K 16/22 |
| 2018/0161274 A1* | 6/2018 | Vogelstein | A61K 9/1271 |

FOREIGN PATENT DOCUMENTS

| | | |
|---|---|---|
| RU | 2574926 C9 | 6/2020 |
| WO | 1988006442 A1 | 9/1988 |
| WO | 96/00057 A1 | 1/1996 |
| WO | 03/032947 A2 | 4/2003 |
| WO | 2005/107712 A1 | 11/2005 |
| WO | 2005107712 A1 | 11/2005 |
| WO | 2010113984 A1 | 10/2010 |
| WO | 2010143972 A2 | 12/2010 |
| WO | 2016/131006 A1 | 8/2016 |

OTHER PUBLICATIONS

International Search Report in PCT/SG2018/050026 dated Feb. 15, 2018, 5 pages.
Rudolph et al., "BI 6727, A Polo-like Kinase Inhibitor with Improved Pharmacokinetic Profile and Broad Antitumor Activity," Clinical Cancer Research, 2009, vol. 15, No. 9, pp. 3094-3102.
Sontakke and Fulzele, "Cytogenetic study on genotoxicity of antitumor-antibiotic Mitomycin C," Biomedical Research, 2009, vol. 20, No. 1, pp. 40-44.
Sur et al., "Remote loading ofpreencapsulated drugs into stealth liposomes," Proceedings of the National Academy of Sciences, 2014, vol. 111, No. 6, pp. 2283-2288.
Opposition to Colombian Patent Application No. NC2019/0008876, with an English Translation, Jan. 17, 2020, 17 pages.
European Search Report issued in European Application No. EP 18 74 1815, dated Sep. 28, 2020, 11 pages.
Office Action issued in corresponding Indonesian Patent Application No. P-00201907098, dated Apr. 13, 2021, 2 pages.
Office Action issued in corresponding Chinese Patent Application No. 201880012370.3, dated Apr. 13, 2021, with an English Translation, 21 pages.
Office Action issued in corresponding Russian Patent Application No. 2019125724, dated Mar. 4, 2021, with an English Translation, 17 pages.
Kacoli Banerjee et al., Liposomes as a drug delivery system /Biological and Pharmaceutical Applications of Nanomaterials, 2015, pp. 55-100.
Office Action issued in corresponding Colombian Patent Application No. NC2019/0008876, dated Jul. 13, 2021, 15 pages, with an English Translation.
Qiao Yuan, et al., "A Robust Approach to Enhance Tumor-selective Accumulation of Nanoparticles", Oncotarget, vol. 2, No. 1-2, Mar. 1, 2011, pp. 59-68.

* cited by examiner

HYPERSTABILIZED LIPOSOMES INCREASE TARGETING OF MITOTIC CELLS

The present application is a national stage filing under 35 U.S.C. § 371 of PCT/SG2018/050026, filed on Jan. 17, 2018, which is related to and claims the benefit of priority to U.S. Provisional Patent Application Ser. No. 62/447,498, filed Jan. 18, 2017. Each application is incorporated herein by reference in its entirety.

BACKGROUND OF THE INVENTION

The present invention relates to the field of cancer treatment. More specifically, the invention relates to hyperstable liposomes useful for the treatment of cancer and to methods of treating cancer using the hyperstable liposomes.

The publications and other materials used herein to illuminate the background of the invention or provide additional details respecting the practice, are incorporated by reference, and for convenience are respectively grouped in the Bibliography.

If cancer is fundamentally a state of excessive cell division, then mitosis-regulating enzymes should make great anticancer drug targets. Indeed, it was the success of microtubule targeting agents (MTAs) as a drug class which motivated the search for more specific ways of inhibiting mitosis, hence avoiding the peripheral neuropathy associated with MTAs [1-3]. Enzymatic regulators which played a pivotal role in mitosis such as the Polo-like Kinases (PLK) [4,5], Kinesin-Spindle Protein (KSP)[6,7] and Aurora kinases [8,9] immediately became high priority drug targets. However, despite more than $10 billion spent on the development of 25 mitosis-specific agents, performance has been dismal with no reported clinical efficacy [10,11].

However, mitosis-regulating enzymes may be inherently bad drug targets because only a limited proportion of tumor cells are actually dividing at any one time. As concisely stated by Komlodi-Pasztor et al [10], "for a targeted therapy to be effective, the target must be present." This argument implies however that mitotic-regulating enzymes can perhaps still be efficacious if tumor bioavailability can be temporally sustained. The fact that preclinical testing of the PLK inhibitor BI 2536 only showed tumor reduction with bi-weekly administration [4] supports the idea that sustained bioavailability increases the chance of catching a tumor cell in the act of cell division.

Liposomes are well known colloidal particles that have been used for drug delivery. It is well-known that small molecules, including drugs, may be "remotely loaded" into liposomes by creating a physicochemical differential between the internal and external environment of the liposome [16-18]. Importantly, the drug should be membrane permeant in the external environment but become charged and hence entrapped upon diffusing into the internal environment. If the drug is a weak base, one way to create this differential is to encapsulate buffering anions in the liposome interior which create a low pH relative to the exterior.

Liposomes are known to exploit fenestrations in tumor endothelium to access and persist in tumor tissues [12,13]. This phenomenon, called the Enhanced Permeability and Retention (EPR) effect was first demonstrated with doxorubicin, resulting in the liposomal cancer drug Doxil™[14,15]. It turns out that the stability of liposomal encapsulation is a double-edge sword as demonstrated by Doxil™. On the one hand, drug exposure to healthy tissue is reduced. On the other hand, the slow leakage of doxorubicin from liposomes places a brake on efficacy because most cancer drugs require high tumoral concentrations to be effective.

In contrast to doxorubicin, BI 2536 is effective at $1000^{th}$ the concentration of doxorubicin, implying that sustained exposure and not maximal concentration should greatly enhance efficacy.

It is desired to develop systems which would maximize the temporal exposure of a mitosis inhibiting agent in order to increase the fraction of dividing cancer cells which can be targeted by the mitosis inhibiting agent.

SUMMARY OF THE INVENTION

The present invention relates to the field of cancer treatment. More specifically, the invention relates to hyperstable liposomes useful for the treatment of cancer and to methods of treating cancer using the hyperstable liposomes.

Thus, in one aspect, the present invention provides hyperstable liposomes encapsulating an anti-mitotic drug. In some embodiments, the anti-mitotic drug is BI 2536, Ispinesib (SB 715992), MK 0457 (VX 680), AZD 1152, PHA 680632, PHA 739358, MLN8054, MLN8237, R763, AT9283, SNS 314, SU 6668, ENMD 2076, BI 811283, CYC116, ENMD 981693, MKC 1693, ON01910, GSK 461364, HMN 214, BI 6727, SB 743921, MK 0731 or ARRY 520. In some embodiments, any suitable liposomal constituent can be used to prepare the hyperstable liposomes. In some embodiments, the hyperstable liposomes are sterically stabilized. In some embodiments, the hyperstable liposomes are prepared from a lipid mixture comprising HEPC:Chol:DSPE-PEG2000 (HEPC: Hydrogenated Egg L-α-Phosphatidy-lcholine; Chol: Cholesterol; DSPE-PEG-2000: 1,2-Distearoyl-sn-Glycero-3-Phosphoethanol-amine-N-[Methoxy (Polyethylene glycol)-2000] in the molar ratio 50:45:5. In some embodiments, the hyperstable liposomes contain an inner milieu having one or more anions, preferably two or more anions, which provide for a slow release of the anti-mitotic agent from the hyperstable liposomes. In some embodiments, the one or more anions, or preferably two or more anions, may be as described herein. In some embodiments, the inner milieu contains one or more cations. In some embodiments, the one or more cations may be as described herein. The best combination of anions and cations can be readily determined for a given anti-mitotic drug by using the techniques described herein.

In some embodiments, a pharmaceutical composition is provided which comprises the hyperstable liposomes described herein with or without at least one pharmaceutically acceptable excipient and/or carrier. Suitable pharmaceutically acceptable excipients and carriers are well known in the art.

In a second aspect, the present invention provides a method of treating cancer using the hyperstable liposomes described herein. According to this method, a therapeutically effective amount of hyperstable liposomes are administered to a patient, e.g., human, in need of treatment.

BRIEF DESCRIPTION OF THE FIGURES

FIG. 5A: Scatter plots of $EC_{50}$ vs. release rate measured on days 3 and 8 for various citrate:phosphate (C:P) ratios are shown. FIG. 5B: Mice xenografted with HCT116 colorectal cancer cells were treated with a single dose of liposomal BI 2536 formulated at various C:P ratios. 3 mice were used for each experimental arm. Tumor volumes and weights are reported. Error bars indicate standard errors.

(FIG. 7A): Mice bearing HCT116 xenografts were treated with BI 2536 encapsulated using various citrate:phosphate ratios. Each data point comprises 3 mice. BI 2536 was extracted from tissues at various time points quantified by fluorometry. Data points and error bars represent means and standard errors respectively. Significant differences (p<0.05) between hyperstable liposomes (C:P=1:3) and the other groups are indicated with asterisks. (FIG. 7B): Tissue exposure to BI 2536 as measured by area under curve is shown. (FIG. 7C): The percentage of mitotically arrested cells at 1.5 and 5.5 days post-treatment is shown. Each bar is derived from 6 separate visual fields of 2 non-adjacent H&E stained sections. Error bars represent standard errors. (FIG. 7D): Typical H&E images are shown for the various treatments. Arrows point to examples of mitotically arrested cells. Scale bar, 10 μm.

DETAILED DESCRIPTION OF THE INVENTION

Figure 1:
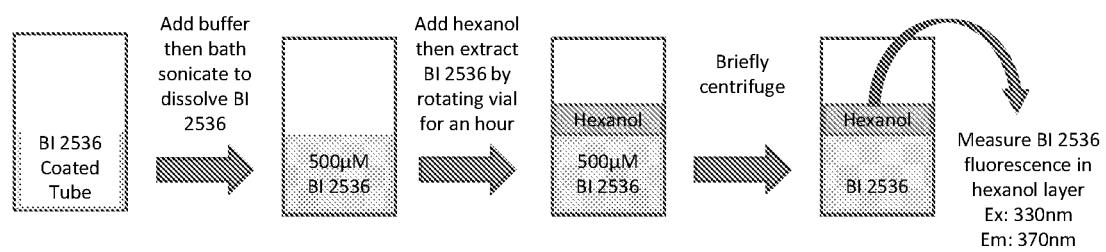
FIG. 1 shows a procedure for studying the ability of BI 2536 to partition from various salt solutions into hexanol.

The present invention relates to the field of cancer treatment. More specifically, the invention relates to hyperstable liposomes useful for the treatment of cancer and to methods of treating cancer using hyperstable liposomes. It has been discovered that extreme prolongation of mitosis-inhibiting drug release from hyperstable liposomes improves efficacy in treating cancer by increasing the proportion of targetable cancer cells. The slow release of the mitosis-inhibiting drug from hyperstable liposomes is correlated with in vitro and in vivo cancer cell killing. In one example, xenografted mice treated with a single dose of hyperstable liposomal BI 2536 experienced tumor volume decreases lasting 12 days and complete responses in 20% of the treated mice. Treatment with two doses a week apart increased the response rate to 75% of the treated mice.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

As used herein, "cancer" refers to a group of diseases involving abnormal cell growth with the potential to invade or spread to other parts of the body. Cancers include carcinomas, such as glioma, head and neck, kidney, lung, medulloblastoma, melanoma, Merkel cell carcinoma, mesothelioma, neuroblastoma, oesophagus, ovary, pancreas, prostate, stomach, testis, thyroid; leukemias such as acute myeloid leukemia, chronic myeloid leukemia, hairy cell leukemia, lymphoblastic T-cell leukaemia, T-cell leukemia, B-cell leukemia; lymphomas such as anaplastic large cell lymphoma, B-cell lymphoma, Burkitt lymphoma, Hodgkin lymphoma; and myelomas.

The term "mitosis-inhibiting drug" means a drug that targets mitosis regulating enzymes, such as mircrotubule regulating enzymes, Polo-like Kinases (PLK), Kinesin-Spindle Protein (KSP), Aurora kinases, and the like. The term "anti-mitotic drug" or "anti-mitosis drug" may be used interchangeably with "mitosis-inhibiting drug."

As used herein, "hyperstable liposome" refers to liposome-encapsulated drug having a slow release of the drug due, in part, to the anions and cations present in the interior milieu of the liposome. The slowest rate of release for the hyperstable liposomes are highly correlated with cancer cell killing.

The term "slow release of drug" refers to the quantified release of a drug from a liposome-encapsulated drug that is less than 0.6% in 12 hours or less than 5% in 8 days when the liposomes are suspended in 600 mM sucrose.

In one aspect, the present invention provides hyperstable liposomes encapsulating an anti-mitotic drug. In some embodiments, the anti-mitotic drug is a polo-like kinase inhibitor, such as BI 2536, ON01910, GSK 461364, HMN 214 or BI 6727. In other embodiments, the antimitotic drug is a kinesin spindle inhibitor, such as Ispinesib (SB 715992), SB 743921, MK 0731 or ARRY 520. In some embodiments, the anti-mitotic agent is a aurora kinase inhibitor, such as MK 0457 (VX 680), AZD 1152, PHA 680632, PHA 739358, MLN8054, MLN8237, R763, AT9283, SNS 314, SU 6668, ENMD 2076, BI 811283, CYC116, ENMD 981693 or MKC 1693. In some embodiments, the anti-mitotic agent is BI 2536 or Ispinesib.

In some embodiments, any suitable liposomal constituent can be used to prepare the hyperstable liposomes. In some embodiments, the hyperstable liposomes are sterically stabilized. In some embodiments, the hyperstable liposomes are prepared from a lipid mixture comprising HEPC:Chol: DSPE-PEG2000 (HEPC: Hydrogenated Egg L-α-Phosphatidy-lcholine; Chol: Cholesterol; DSPE-PEG-2000: 1,2-Distearoyl-sn-Glycero-3-Phosphoethanol-amine-N-[Methoxy (Polyethylene glycol)-2000] in the molar ratio 50:45:5.

In some embodiments, the hyperstable liposomes contain an inner milieu having one or more anions, preferably two or more anions, which provide for a slow release of the anti-mitotic agent from the hyperstable liposomes. In some embodiments, the one or more anions, or preferably two or more anions, may be citrate, acetate, phosphate, 2-(N-morpho-lino)ethanesulfonate, chloride, citrate and acetate, citrate and 2-(N-morpholino)ethanesulfonate, citrate and chloride, acetate and phosphate, acetate and 2-(N-morpholino)ethanesulfonate, acetate and chloride, phosphate and 2-(N-morpholino)ethanesulfonate, phosphate and chloride, 2-(N-morpholino)ethanesulfonate and chloride. In some embodiments, the chloride in the form of HCL. In some embodiments, the ratio of two anions may be about 1:7 to about 7:1. In other embodiments, the ratio of two anions may be about 1:3 to about 3:1. In some embodiments, the anions are citrate:phosphate in a ratio of about 1:3 to about 1:7, preferably about 1:3. In some embodiments, the anions are citrate:acetate in a ratio of about 1:3 to about 3:1, preferably about 1:3. In some embodiments, the inner milieu contains one or more cations. In some embodiments, the one or more cations may be sodium, ammonium, triethylammonium, copper, magnesium, zinc or iron. The best combination and ratios of anions and cations can be readily determined for a given anti-mitotic drug experimentally in mice, such as by using the techniques described herein.

In some embodiments, the hyperstable liposomes of the present invention can contain one or more anions of the present invention in any suitable form, e.g., in the form of an acid or a salt comprising a polyanion and a cation, preferably as a salt. The amount of anion can be stoichiometrically equivalent to or different from the amount of the cation. In some embodiments, the hyperstable liposome of the present invention contains one or more anion salts of a cation, wherein there is a cation concentration gradient or a pH gradient present across the liposome membrane. In another embodiment, the hyperstable liposome of the present invention contains one or more ammonium anion salts of the present invention. In yet another embodiment, the hyperstable liposomes of the present invention contains the anions inside the hyperstable liposomes while the anions in the medium containing the hyperstable liposomes is partially or substantially removed by any suitable means known to one skilled in the art, e.g., dilution, ion exchange chromatography, size exclusion chromatography, dialysis, ultrafiltration, absorption, precipitation, etc. In some embodiments, the hyperstable liposome with entrapped anion(s), also has a transmembrane gradient effective in retaining substances within the hyperstable liposome. Examples of such transmembrane gradients are pH gradient, electrochemical potential gradient, cation ion gradient, or solubility gradient. Methods of creating transmembrane gradients are routine in the art of liposomes.

In some embodiments, the hyperstable liposomes gain entry into target cells by exploiting fenestrations in tumor endothelium. In other embodiments, the hyperstable liposomes of the present invention can also be targeting liposomes, e.g., liposomes containing one or more targeting moieties or biodistribution modifiers on the surface of the liposomes. A targeting moiety can be any agent that is capable of specifically binding or interacting with a desired target. In some embodiments, a targeting moiety is a ligand. In some embodiments, the ligand preferentially binds to and/or internalizes into, a cell in which the liposome-entrapped entity exerts its desired effect (a target cell). A ligand is usually a member of a binding pair where the second member is present on or in a target cells or in a tissue comprising the target cell. See, e.g., U.S. Pat. No. 8,922,970, incorporated herein by reference.

Liposomes of the present invention can be made by any suitable method known to or later discovered by one skilled in the art. See, for example, Gregoriadis [25], U.S. Pat. Nos. 8,992,970 and 9,023,384, each incorporated herein by reference. Liposomes are typically manufactured using various procedures in which water soluble (hydrophilic) materials are entrapped by using aqueous solution of these materials as hydrating fluid or by the addition of drug/drug solution at some stage during the manufacture of the liposomes. The lipid soluble (lipophilic) materials are solubilized in the organic solution of the constitutive lipid and then evaporated to a dry drug containing lipid film followed by its hydration. These methods involve the loading of the entrapped agents before or during the manufacturing procedure (passive loading). However, certain type of compounds with ionizable groups, and those which display both lipid and water solubility, can be introduced into the liposomes after the formation of intact vesicles (remote or active loading).

When preparing liposomes with mixed lipid composition, the lipids are first dissolved and mixed in an organic solvent to assure a homogeneous mixture of lipids. In some embodiments, the organic solvent is chloroform or chloroform: methanol mixtures. Once the lipids are thoroughly mixed in the organic solvent, the solvent is removed to yield a lipid film. In some embodiments, the organic solvent is removed by rotary evaporation at reduced pressure yielding a thin lipid film on the sides of a round bottom flask. The lipid film is typically thoroughly dried overnight under a high vacuum to remove residual organic solvent. Hydration of the dry lipid film is accomplished simply by adding an aqueous buffer solution to the container of dry lipid and agitating at a temperature above the lipid transition temperature. This method yields a population of multilamellar liposomes (MLVs) heterogeneous in both size and shape (e.g., 1-5 μm in diameter. Liposome size reduction techniques, such as sonication for single unilamellar vesicles (SUVs) formation or extrusion through polycarbonate filters forming large unilamellar vesicles (LUVs). Additional details and further methods for the preparation of liposomes with encapsulated drugs can be found in Fritze et al. [16], Dua et al. [20], Laouini et a. [21], U.S. Pat. Nos. 8,992,970 and 9,023,384, each incorporated herein by reference.

In some embodiments, the hyperstable liposomes of the present invention are formulated at the nanoscale using saturated phosphatidylcholine coupled with high cholesterol content to decrease membrane permeability. In some embodiments, the hyperstable liposomes are further formulated using PEGylation or other conjugation for steric-stabilization. In other embodiments, the saturated phosphatidylcholine can be replaced by other membrane forming phospholipids. In some embodiments, the hyperstable liposomes are prepared using conventional techniques or those described herein. In some embodiments the membrane forming phospholipids is a saturated phosphatidylcholine (PC), any synthetic phosphatidylcholine (PC) with saturated fatty acid tails, or membrane forming lipids. In some embodiments, synthetic PC may be dimyristoyl-phosphatidylcholine, dipalmitoyl-phosphatidylcholine, or distearoyl-phosphatidylcholine. In some embodiments, the saturated phosphatidylcholine (PC) is hydrogenated egg yolk phophatidylcholine (HEPC). In other embodiments, the membrane forming lipid may be saturated sphingomyelin, saturated phosphatidylethanolamine, saturated phosphatidylglycerol, saturated phosphatidylinositol or saturated phosphatidylserine.

In some embodiments, the conjugate may be polyethylene glycol, polypropylene glycol, polybutylene glycol, or a copolymer of polyalkylene glycols such as a block copolymer of polyethylene glycol and polypropylene glycol), dextran, pullulan, ficoll, polyvinyl alcohol, styrene-maleic anhydride alternating copolymers, divinyl ether-maleic anhydride alternating copolymers, amylose, amylopectin, chitosan, mannan, cyclodextrin, pectin or carrageenan. In some embodiments, polyethylene glycol (PEG) is used as a conjugate (C-PEG). In some embodiments, the PEG has a molecular weight ranging from about 500 to about 10,000, preferably from about 1,000 to about 5,000, more preferably about 2,000.

In some embodiments, PEG or other conjugate is conjugated with distearoyl phosphatidylethanolamine (DSPE), dipalmitoyl phosphatidylethanolamine (DPPE), dimyristoyl phosphatidylethanolamine (DMPE), distearoyl glycerol (DSG), dimyristoyl glycerol (DMG), cholesterylated-conjugate, Stearyl (STR) conjugate, C8 ceramide-conjugate or C16 ceramide-conjugate. In some embodiments, the conjugate is PEG2000 and the conjugate is DSPE-PEG2000, DPPE-PEG2000, DMPE-PEG2000, DSG-PEG2000, DMG-PEG2000, cholesterylated-PEG2000, STR-PEG2000, C8 ceramide-PEG2000 or C16 ceramide-PEG2000.

In some embodiments, the sterically-stabilized liposomes are prepared from a preparative mixture of PC:cholesterol: C-PEG in which the molar ratio of PC:cholesterol is typically in the range of 2:1 to 1:1 with C-PEG typically present at 5% (mol/mol). In some embodiments, the preparative mixture of PC:cholesterol:C-PEG has a molar ratio of 50:45: 5. In some embodiments, the preparative mixture is HEPC: cholesterol:DSPE-PEG2000. In some embodiments, the preparative mixture of HEPC:cholesterol:DSPE-PEG2000 has a molar ratio of 50:45:5.

In some embodiments, the liposomes are prepared by solubilizing the preparative mixture described herein in chloroform. This solution is dried to a thin film under rotary evaporation and then under vacuum overnight. The film is hydrated with a hydration buffer containing the desired salt solution, such as described herein, as the internal milieu of the liposome and submerged in a water bath sonicator. The liposome mixture is first sonicated and subsequently extruded to form SUVs. In some embodiments, the SUVs are dialyzed against sucrose to change the exterior milieu of the liposomes In some embodiments, mitosis-inhibiting drug is actively loaded into the liposomes via a pH gradient method well known in the art. In some embodiments, the mitosis-inhibiting drug is first coated as a thin film in a suitable vessel and subsequently dried. In some embodiments, the liposomes are loaded at a 3:1, lipid:drug concentration and diluted to this desired concentration with water. The mixture was then incubated in a high temperature water bath to facilitate loading and subsequently dialyzed in sucrose to remove un-encapsulated drug.

In some embodiments, the hyperstable liposomes of the present invention are prepared as follows. A lipid mixture of HEPC:Chol:DSPE-PEG2000 in the molar ratio 50:45:5 is dissolved in chloroform. The mixture is dried to a thin lipid film in a round bottom flask under rotary evaporation and further dried under high vacuum overnight before hydration with the desired salt solution as the internal milieu of the liposome. The resulting 100 mM lipid suspension is sonicated with a bath sonicator for 1 hour and subsequently extruded ten times using a Lipex Thermobarrel Extruder through doubly stacked 100 nm Nuclepore filters to form Single Unilamellar Vesicles (SUVs). These SUVs are dialyzed in 300 mM sucrose at 4° C. with three changes of fresh sucrose solution within 24 hours to exchange the exterior milieu of the liposomes. Liposomes are stored in glass tubes at 4° C. until intended use.

In one example, the mitosis-inhibiting drug BI 2536 is actively loaded into liposomes via the pH gradient method. BI 2536 is first coated as a thin film in a scintillation vial by dissolving in ethanol and subsequently drying under rotary evaporation. The BI 2536 film is further dried under vacuum for at least 24 h. The liposomes are loaded at a 3:1, lipid:drug concentration and diluted to a final concentration of about 50 to about 70 mM lipids with water. The mixture is then incubated in a 70° C. water bath to facilitate loading and subsequently dialyzed in 300 mM sucrose for at least 36 h to remove un-encapsulated BI 2536. After dialysis, liposomes are stored in glass tubes until usage.

In some embodiments, the hyperstable liposomes of the present invention are quite stable during storage, e.g., as measured by the percentage of entrapped entity released outside of the hyperstable liposomes or still maintained inside of the hyperstable liposomes after a certain time period from the initial loading of the entity inside the hyperstable liposomes of the present invention. For example, the hyperstable liposome composition of the present invention is stable at 4° C. for at least 6 months.

It is advantageous for a liposome-entrapped anti-mitotic agent to remain encapsulated in the liposome until the hyperstable liposome reaches the site of its intended action, e.g., in the case of a liposomal anti-mitotic drug administered in a patient, a tumor. The hyperstable liposomes of the present invention showed surprising stability against the release (leakage) of the entrapped anti-mitotic drug under in vivo conditions, e.g. in the blood of a mammal. Remarkably, the hyperstable liposomes of the present invention, while having such low in vivo drug release rate in the blood circulation, showed substantial in vitro antitumor activity. The hyperstable liposomes of the present invention provided unexpected combination of the high efficacy of the entrapped anti-mitotic drug and low toxicity.

In some embodiments, a liposomal composition is provided which comprises hyperstable liposomes described herein in an aqueous medium. In some embodiments, the hyperstable liposomes have an interior aqueous space separated from the aqueous medium by a membrane. In some embodiments, the membrane comprises 1,2-distearoyl-sn-glycerol-3-phosphoethanolamine-N-[methoxy (polyethylene glycol)-2000], hydrogenated egg L-α-phosphatidylcholine and cholesterol. In some embodiments, entrapped inside the hyperstable liposomes are an anti-mitotic drug, anion(s) and cation(s) in which the anti-mitotic drug entrapped inside the hyperstable liposomes is at a concentration that exceeds the concentration of the anti-mitotic drug in the aqueous medium.

In some embodiments, a pharmaceutical composition is provided which comprises hyperstable liposomes described herein with or without at least one pharmaceutically acceptable excipient and/or carrier. In some embodiments, pharmaceutically acceptable carries are normal saline, isotonic dextrose, isotonic sucrose, Ringer's solution, and Hanks' solution. A buffer substance can be added to provide pH optimal for storage stability. For example, pH between about 6.0 and about 7.5, more preferably pH about 6.5, is optimal for the stability of liposome membrane lipids, and provides for excellent retention of the entrapped entities. Histidine, hydroxyethylpiperazine-ethylsulfonate (HEPES), morpholipo-ethylsulfonate (YMS), succinate, tartrate, and citrate, typically at 2-20 mM concentration, are exemplary buffer substances. Other suitable carriers include, e.g., water, buffered aqueous solution, 0.4% NaCl, 0.3% glycine, and the like. Protein, carbohydrate, or polymeric stabilizers and tonicity adjusters can be added, e.g., gelatin, albumin, dextran, or polyvinylpyrrolidone. The tonicity of the composition can be adjusted to the physiological level of 0.25-0.35 mol/kg with glucose or a more inert compound such as lactose, sucrose, mannitol, or dextrin. These compositions may be sterilized by conventional, well known sterilization techniques, e.g., by filtration. The resulting aqueous solutions may be packaged for use or filtered under aseptic conditions and lyophilized, the lyophilized preparation being combined with a sterile aqueous medium prior to administration.

In some embodiments, pharmaceutically acceptable excipients may be used as required to approximate physiological conditions, such as pH adjusting and buffering agents, tonicity adjusting agents and the like, for example, sodium acetate, sodium lactate, sodium chloride, potassium chloride, calcium chloride, etc. Additionally, the hyperstable liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The concentration of the hyperstable liposomes of the present invention in the pharmaceutical compositions can vary widely, i.e., from less than about 0.05% usually or at least about 2-10% to as much as 30 to 50% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, pharmaceutical compositions composed of irritating lipids may be diluted to low concentrations to lessen inflammation at the site of administration.

In a second aspect, the present invention provides a method of treating cancer using the hyperstable liposomes described herein. In some embodiments, the amount of hyperstable liposome pharmaceutical composition administered will depend upon the particular anti-mitotic drug entrapped inside the hyperstable liposomes, the cancer being treated, the type of hyperstable liposomes being used, and the judgment of the clinician. Generally the amount of hyperstable liposome pharmaceutical composition administered will be sufficient to deliver a therapeutically effective dose of the particular anti-mitotic drug.

The quantity of hyperstable liposome pharmaceutical composition necessary to deliver a therapeutically effective dose can be determined by routine in vitro and in vivo methods, common in the art of drug testing. See, for example, Budman et al. [22]. Therapeutically effective dosages for various anti-mitotic drugs are well known to those of skill in the art; and according to the present invention an anti-mitotic drug delivered via the pharmaceutical composition of the present invention provides at least the same, or 2-fold, 4-fold, or 10-fold higher activity than the activity obtained by administering the same amount of the anti-mitotic drug in its routine non-liposome formulation. Typically the dosages for the hyperstable liposome pharmaceutical composition of the present invention range between about 0.005 and about 500 mg of the therapeutic entity per kilogram of body weight, most often, between about 0.1 and about 100 mg therapeutic entity/kg of body weight.

Typically, the pharmaceutical composition of the present invention is prepared as a topical or an injectable, either as a liquid solution or suspension. However, solid forms suitable for solution in, or suspension in, liquid vehicles prior to injection can also be prepared. The composition can also be formulated into an enteric-coated tablet or gel capsule according to known methods in the art.

The hyperstable liposome composition of the present invention can be administered in any way which is medically acceptable which may depend on the cancer being treated. Possible administration routes include injections, by parenteral routes such as intramuscular, subcutaneous, intravenous, intraarterial, intraperitoneal, intraarticular, intraepidural, intrathecal, or others, as well as oral, nasal, ophthalmic, rectal, vaginal, topical, or pulmonary, e.g., by inhalation. For the delivery of liposomally anti-mitotic drugs formulated according to the invention, to tumors of the central nervous system, a slow, sustained intracranial infusion of the liposomes directly into the tumor (a convection-enhanced delivery, or CED) is of particular advantage. See Saito et al. [23] and Mamot et al. [24]. The compositions may also be directly applied to tissue surfaces. Sustained release, pH dependent release, or other specific chemical or environmental condition mediated release administration is also specifically included in the invention, e.g., by such means as depot injections, or erodible implants.

Figure 8A:
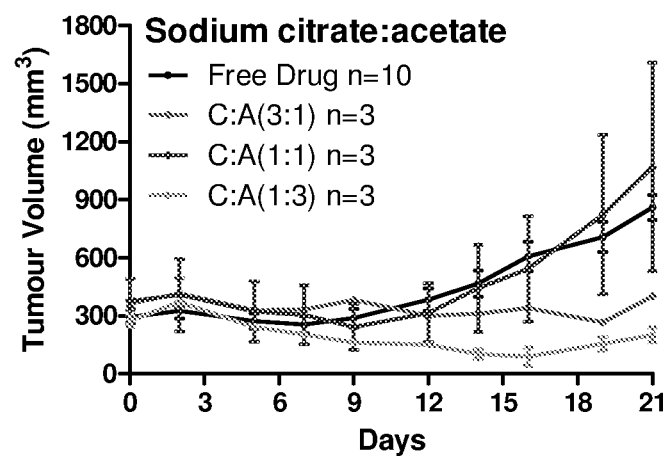
FIGS. 8A and 8B show in vivo efficacy of liposomal BI 2536 on HCT116 xenografted mice. Tumor volumes are shown for single dose treatment at day 0 with (FIG. 8A) liposomes formulated with varying ratios of citrate:acetate and (FIG. 8B) liposomes formulated with varying ratios of citrate:acetate but with the sodium cation replaced by ammonium. All formulations were administered at 340 mg/kg of BI 2536. Error bars represent standard errors.
Figure 8B:
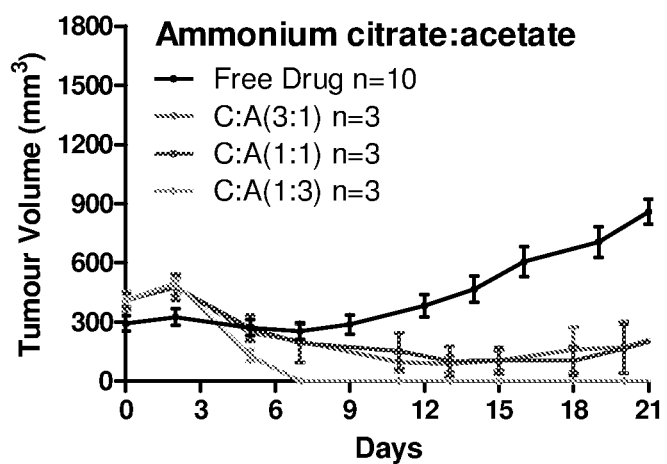

As shown in the following Examples, an approach using combinatorial anion diversity to identify slow-releasing hyperstable liposomal formulations is described. Although the citrate:phosphate anion pair was focused on in the Examples, other hyperstable anion pairs found in the screen (FIG. 4) will also produce similar results for BI 2536. When the citrate:phosphate pair was replaced with citrate:acetate, mice treated with a single dose of this alternative liposomal version exhibited similar efficacy with the citrate:acetate ratio of 1:3 producing the greatest tumor reduction (FIG. 8A). A natural means of adding even greater diversity is to vary cation identity. For instance, replacing the sodium cation with ammonium for the citrate:acetate pair dramatically increases the rate of tumor regression (FIG. 8B).

Hyperstable liposomes solve two conceptual problems. Prolonging temporal availability allows an antimitotic drug to catch more tumor cells in the act of replication. Further, the low persisting drug concentration achieved by hyperstable liposomes is less likely to trigger mitotic slippage [19]. This means that fewer tumor cells should escape the intended effects of the drug. This approach can be applied to any anti-mitotic drug, not just BI 2536. Hence, hyperstable encapsulation has the potential to revive the clinical utility of 24 drugs which fall within this class. One advantage of the hyperstable liposomes is prolonging bioavailability on the time scale of two weeks for a single dose which will enable clinicians to achieve higher efficacy with less frequent dosings. Another advantage is the lack of irreversible neuropathy after treatment with the hyperstable liposomes compared to other drug classes which is an attractive feature of mitotic inhibitors from a toxicity standpoint. The description of a general method for reactivating failed mitosis inhibitors opens the door to many possibilities and demonstrates that it is not the idea of inhibiting mitosis that is flawed; it's the delivery which matters.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Liposome Preparation:
1,2-Di stearoyl-sn-Glycero-3-Phosphoethanolamine-N-[Methoxy (Polyethylene glycol)-2000] (DSPE-PEG2000) and Hydrogenated Egg L-α-Phosphatidylcholine (HEPC) were purchased from Lipoid and Cholesterol (Chol) was purchased from Sigma-Aldrich. A lipid mixture of HEPC:Chol:DSPE-PEG2000 in the molar ratio 50:45:5 was dissolved in chloroform (Takara). The mixture was dried to a thin lipid film in a round bottom flask under rotary evaporation (Eyela NVC-2200/N-1100) and further dried under high vacuum overnight before hydration with the desired salt solution as the internal milieu of the liposome. The resulting 100 mM lipid suspension was sonicated with a bath sonicator (S30H Elmasonic) for 1 hour and subsequently extruded ten times using a Lipex Thermobarrel Extruder (Northern Lipids) through doubly stacked 100 nm Nucleopore filters (Whatman) to form Single Unilamellar Vesicles (SUV). These SUVs were dialysed in 300 mM sucrose (Sigma) at 4° C. with three changes of fresh sucrose solution within 24 hours to exchange the exterior milieu of the liposomes. Liposomes were stored in glass tubes at 4° C. until intended use.

Loading of BI 2536 into Liposomes:
BI 2536 (Axon) was actively loaded into liposomes via the pH gradient method. The requisite BI 2536 was first coated as a thin film in a scintillation vial by dissolving in ethanol and subsequently drying under rotary evaporation. The BI 2536 film was further dried under vacuum for at least 24 h. The liposomes were loaded at a 3:1, lipid:drug concentration and diluted to a final concentration of 50 to 75 mM lipids with water. The mixture was then incubated in a 70° C. water bath to facilitate loading and subsequently dialysed in 300 mM sucrose for at least 36 h to remove un-encapsulated BI 2536. After dialysis, liposomes were stored in glass tubes until usage and a portion of the sucrose dialysate was stored at 4° C. for downstream encapsulation efficiency determination.

Determination of BI 2536 Encapsulation:
The amount of BI 2536 loaded into liposomes was determined by direct calculation (in vitro studies) or back calculation (for animal studies). For direct calculation, 1 μl of liposomes was diluted with 20 μl of ethanol and read via fluorometric measurement using 360 nm excitation and 470 nm emission (Tecan Infinite M200). The quantity of BI 2536 was determined by comparison with a standard curve. For back calculation, 100 μl of 1-nonanol (Merck) was used to extract unencapsulated BI 2536 from 1.5 ml of dialysate by vortexing for 1 h. The nonanol and sucrose were phase separated by brief centrifugation and 20 ul of the nonanol layer was measured for fluorometric intensity using 330 nm excitation and 370 nm emission (Tecan Infinite M200). The concentration of BI 2536 in the dialysates was determined by comparison with a standard curve, and the encapsulation efficiency was then calculated by the formula $$\frac{A-B}{A} \times [BI2536]_{initial}$$

where A=[BI 2536 in dialysate]$_{no\ drug\ loaded}$ and B=[BI 2536 in dialysate]$_{sample}$.

Cell Culture:
HCT116 (CCL-247, human colorectal carcinoma) was purchased from the American Type Culture Collection (ATCC) and cultured using McCoy's 5A Medium (Life Technology) supplemented with 10% Fetal Bovine Serum (Thermo Scientific). Cells were incubated at 37° C. with 5% $CO_2$ and passaged every 2 to 3 days when confluence reached ~80%. $EC_{50}$ determination: Approximately 7×10$^3$ HCT116 cells were seeded into 96-well plates, reaching a confluence of ~50% after overnight incubation. Media in the wells was replaced with fresh media supplemented with either free BI 2536 or liposomal BI 2536. The concentrations of BI 2536 used were generated by serially diluting 1 μM BI 2536. Wells containing media only were used as the blank control. At least 3 repeats were performed for each for formulation. SYBR Green I (Life Technologies) was used to quantify DNA as a measure of cell survival. This was done by first incubation the cells with 50$_1$1.1 of 0.2% sodium dodecyl sulphate at 37° C. for 2 h to lyse them. 150 μL SYBR Green solution (1:750 dilution in water) was then added each well and fluorescence intensity (Ex: 497 nm/Em: 520 nm) measured using the Tecan plate reader. Fluorescence intensity values were entered into GraphPad Prism V5. Logistics regression curves and $EC_{50}$ were determined by setting the highest fluorescence value as 100% survival and lowest fluorescence value as 0% survival.

Animal Studies:
All animal experiments were approved by the Institutional Animal Care and Use Committee of Temasek Life Sciences Laboratory and National University of Singapore (NUS).

Female NCr Nude mice (Ages 5-8 weeks) were purchased from (Singapore/InVivos) and subcutaneously xenografted with HCT116 cells. HCT116 cells were grown as described above in 600 cm$^2$ dishes (Corning) and each dish was used to graft 5 mice when confluence reached ~80%.

Efficacy Studies:

Free BI 2536 (dissolved in 0.1 N HCl, saline) or the indicated liposomal BI 2536 formulations were administered by slow tail vein injection 7 days post grafting with HCT116. Tumor volumes were at least 150 mm$^3$ and calculated using length×width$^2$×0.5. All measurements were performed using vernier calipers and mice were weighed every other day. Mice were subcutaneously hydrated with 1 ml Hartmann's solution daily for 5 days post treatment to ensure that the mice were fully hydrated.

Pharmacokinetics Study:

Mice bearing HCT116 xenografts were treated with indicated free BI 2536 or liposomal BI 2536 formulations and at indicated time points post treatment were euthanized to collect the heart, tumour, muscle, kidney, liver and spleen. Organs were weighed and stored at −80° C. before tissue processing. Tissues were processed by immersion in chaotropic 8M urea (Vivantis) and homogenization in a Bertin Homogenizer using 0.5 mm diameter zirconia beads (Biospec). Homogenized tissues were spun at top speed on a benchtop centrifuge for an hour and 800 µl of the supernatant was collected for extraction of BI 2536 using 100 µl nonanol and gentle rotation for 1 hour. The nonanol and sucrose were phase separated by brief centrifugation and 20 ul of the nonanol layer was read via fluorometric measurement (Ex: 330 nm/Em: 370 nm) using the Tecan plate reader. BI2536 was quantitated by comparison to a standard curve and then normalized against the weight of the tissue.

Histology:

Mice were sacrificed for tumor tissue collection on the indicated post treatment days. Tumor tissues were frozen in OCT medium (Sakura Finetek) and stored at −80° C. before prior to sectioning. 10 µm tumor tissue sections were obtained using a CM3050S cryostat (Leica). Sectioned tissues were fixed in methanol and immediately stained with Hematoxylin and Eosin (H&E). To perform H&E staining, tumor sections were first over stained with filtered Harris solution (Sigma), washed with running tap water, dipped into acid-alcohol (1% hydrochloric acid, 70% ethanol) and further washed with tap water. Tissues sections were then dipped into 0.2% ammonia water (Sigma) until bluing. After washing in tap water for 10 minutes, tissue sections were stained with eosin-phloxine (Sigma and Merck respectively) and dipped in 95% ethanol to wash off excess stain. Tissue sections were dried overnight before mounting with Permount (Fisher). All H&E stained sections were viewed and bright field images were acquired using an Axioplan 2 microscope (Carl Zeiss, Inc) coupled with a DXM 1200F camera (Nikon) and 63× objective.

Preparing BI 2536 in Buffers:

BI 2536 was first dissolved in ethanol and then coated onto 1.5 ml microfuge tubes by spin drying. BI 2636-coated tubes were then further dried overnight under high vacuum before resuspending in the indicated salt solutions to achieve a final concentration of 500 µM. To ensure complete dissolution of coated BI2536, tubes were briefly vortexed and subjected to bath sonication for 1 minute before being used for characterization.

Hexanol Extraction:

BI 2536 from 1 ml of the indicated buffer was extracted with 100 µl 1-hexanol (Merck) by brief shaking for 1 hour. Hexanol and buffer layers were separated by brief centrifugation and 20 ul of the hexanol layer was analyzed for fluorescence intensity using the Tecan plate reader (Ex: 330 nm, Em: 370 nm).

Liposome Stability Assay:

Fluorescence dequenching of leaked BI 2536 was used as a measure of liposomal instability. All fluorescence readings were performed using the Tecan plate reader (Ex: 280 nm, Em: 385 nm). Triton-X100 (sigma) was added to achieve a final concentration of 0.2% to fully release BI 2536 from the liposomes and the fluorescence reading was performed again. To calculate the fraction of BI 2536 released, fluorescence readings before triton addition were divided by fluorescence readings after triton addition. To perform stability measurements, Liposomal formulations were diluted 50× with either water or 600 mM sucrose solution and fluorescence measured using the Tecan plate reader at the start and after 12 hours of incubation at 37° C. using the Tecan plate reader. For long term stability determination, liposomes were stored in a 37° C. incubator after dilution in water or 600 mM Sucrose and fluorescence readings were performed in a similar fashion on indicated days.

Example 2

Release Rates for Liposomal BI 2536 Inversely Correlate with Tumor Cell Killing

Figure 2:
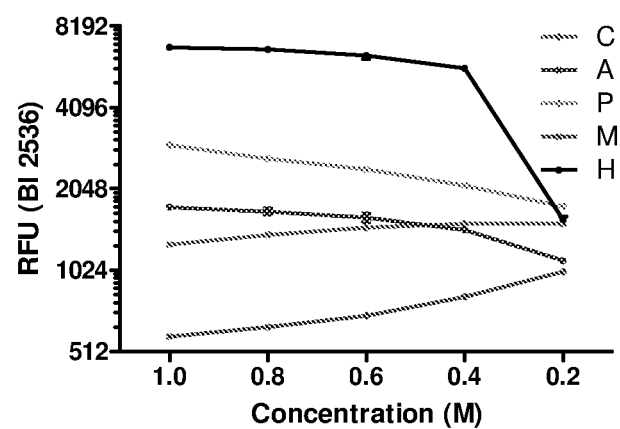
FIG. 2 shows the relative fluorescence of BI 2536 extracted into hexanol from various single anion salt solutions using the methodology described in FIG. 1. BI 2536's partitioning into hexanol and the salt solution is affected by the identity and concentration of the salt anion. The abbreviations used are citrate (C), acetate (A), phosphate (P), 2-(N-morpholino)ethanesulfonate (M) and hydrochloric acid (H). All salt solutions are at 0.8M and adjusted to pH 3 with sodium as the cation. Error bars represent standard errors.
Figure 3:
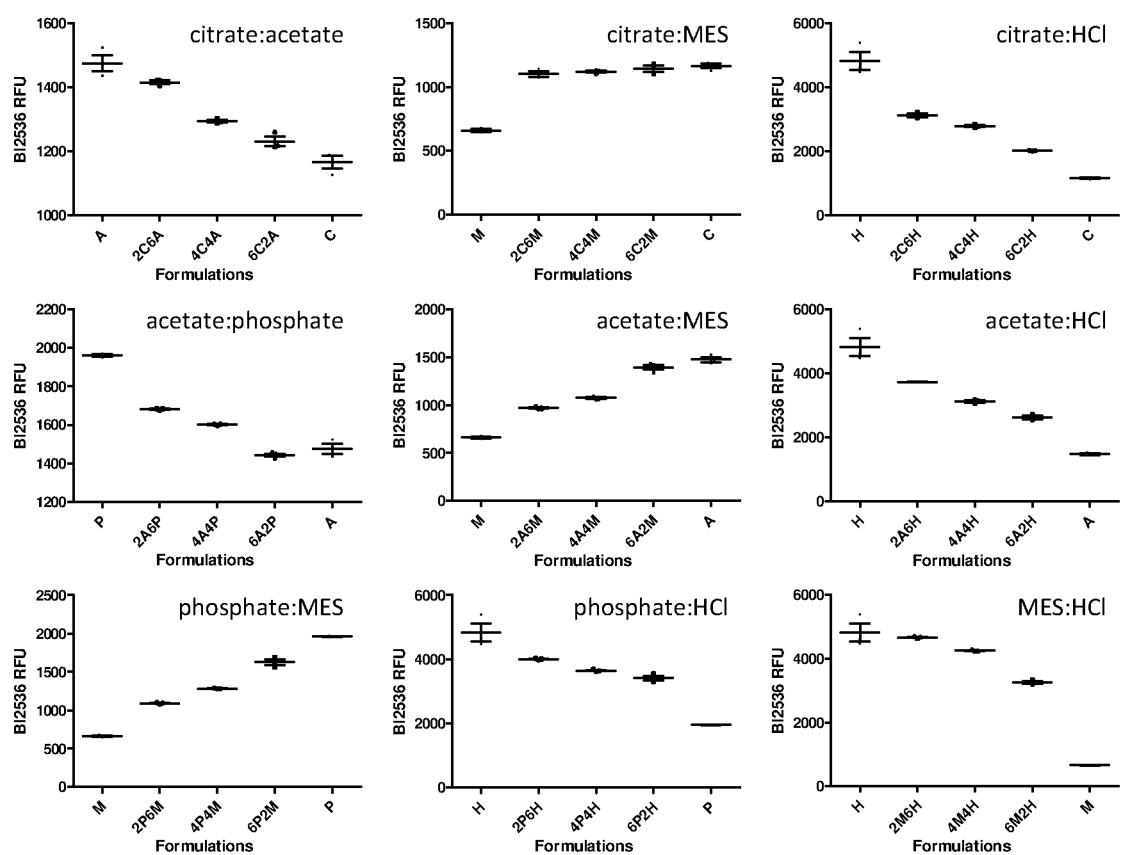
FIG. 3 shows the relative fluorescence of BI 2536 extracted into hexanol from various pairwise anion combinations using the methodology described in FIG. 1. Tuning the molar ratios of the pairwise anion combinations can affect the partitioning of BI 2536 into hexanol. All salts are at 0.8 M and adjusted to pH 3 with sodium as the cation. Single salts have a concentration of 0.8 M. Number before abbreviation represent concentration proportion out of 0.8 M of total salt concentration.

The extent that anion identity and concentration would affect the physicochemical properties of BI 2536 was studied by using the following following solutions adjusted to pH 3: sodium citrate (C), sodium acetate (A), sodium phosphate (P), 2-(N-morpholino)ethanesulfonic acid (M) and hydrochloric acid (H). The tendency of BI 2536 to partition into hexanol from these solutions was measured at various concentrations (FIG. 1). It was observed that anion identity did affect the efficiency of hexanol-extraction and also that this efficiency either increased (P, A) or decreased (M, C, H) in a anion concentration-dependent manner (FIG. 2). It was further observed that the diversity of these hexanol-extraction efficiency curves could be further increased by using pairwise combinations of these anions (FIG. 3). From these results it was reasoned that these anions could be used in a combinatorial manner to create a library of liposomal formulations with varying release rates.

Figure 4:
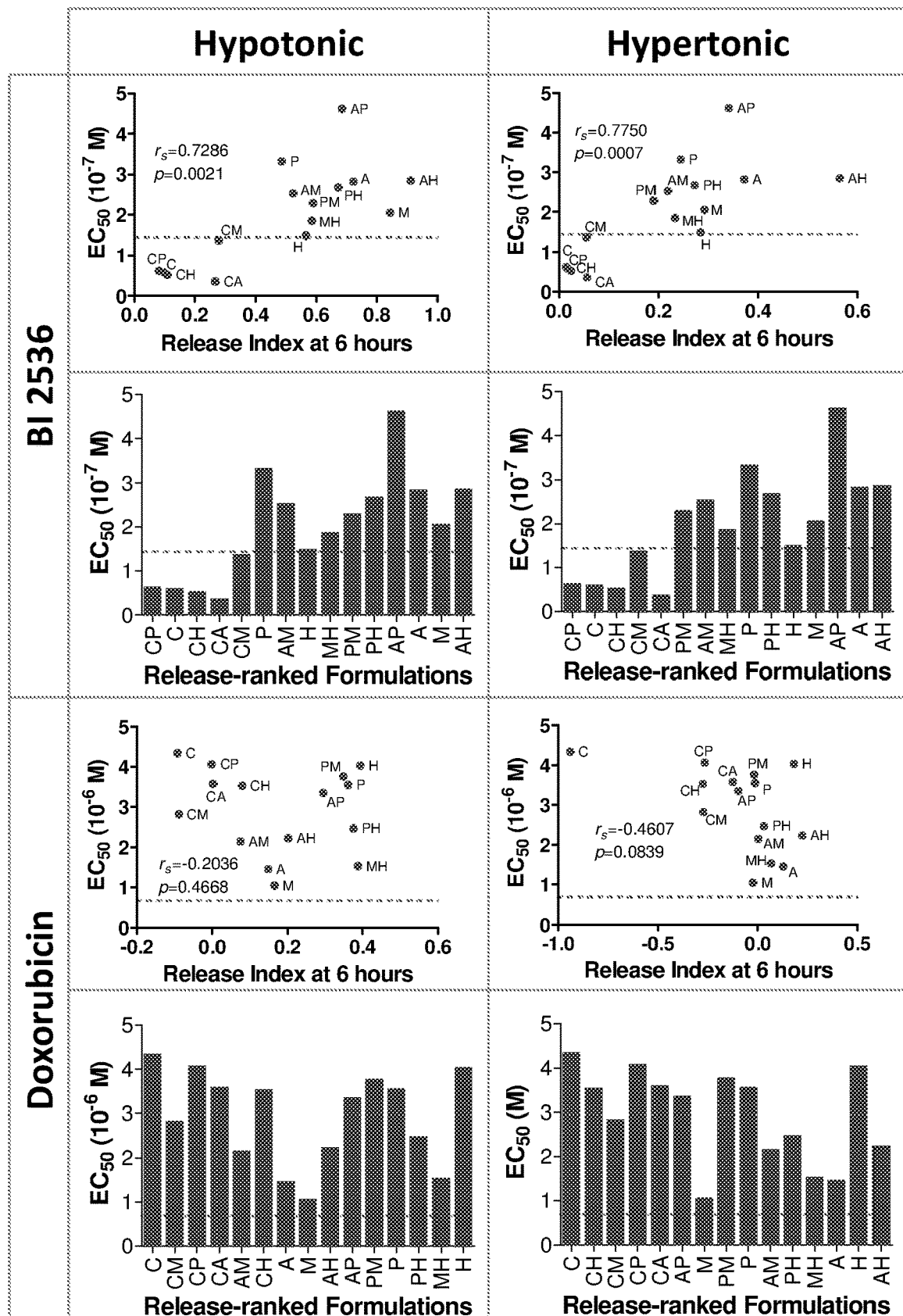
FIG. 4 shows release rates correlate with $EC_{50}$ for liposomal BI2536 but not liposomal Doxorubicin. A continuum of drug release rates was created using single and pairwise combinations of the following anions to perform gradient loading: citrate (C), acetate (A), phosphate (P), 2-(N-morpholino)ethanesulfonate (M) and hydrochloric acid (H). Double-letter abbreviations represent pairwise anion combinations each at half of total concentration. Scatter plots of cytotoxicity ($EC_{50}$) vs. release rates for BI 2536 (top) and Doxorubicin (bottom) are shown for both hypotonic (water) and hypertonic conditions (sucrose). The bar graphs show $EC_{50}$ vs. formulations ranked by release rates for the same data. Dotted lines on all graphs indicate the $EC_{50}$ of unencapsulated drug. Release rates were based on the amount of drug released after 12 hours of incubation. Spearman's rank correlations ($r_s$) and associated p-values are reported.

To identify hyperstable slow-releasing forms of liposomal BI 2536, liposome-encapsulated versions of all 15 single and double combinations of the anions were made and BI 2536 was remotely loaded into their interiors. BI 2536 fluorescence is quenched when encapsulated at high concentrations in the liposome. Hence, the release of BI 2536 from liposomes can be measured by the increase in fluorescence due to dequenching. Using this method, the leakage of BI 2536 for each formulation was measured in hypertonic (600 mM sucrose) and hypotonic (pure water) conditions with respect to time (FIG. 4). As expected, a range of release rates from fast (A, H, AH) to slow (all combinations with citrate) was observed. The rank order of these release rates did not differ appreciably between hypertonic and hypotonic environments, indicating that it is the liposomal internal environment which determines drug release rates for liposomal BI 2536 and not external osmotic stress. To examine if hyperstable slow-releasing liposomes were correlated with cancer cell killing, HCT116 colorectal cancer cells were incubated with serial dilutions of the various liposomal formulations, and their EC$_{50}$ values were calculated as a measure of efficacy. Consistent with the hypothesis that hyperstability was correlated with cytotoxicity, a high correlation between release rates and $EC_{50}$ was found. In contrast, it was found that no similar correlation when the same experiment was performed using doxorubicin (FIG. 4). This finding is consistent with the idea that although mitotic inhibitors might benefit from hyperstability, the opposite would be true for other classes of drugs where slow-release would not be an advantage.

Example 3

Anion Ratios Tune the Release Rate and In Vivo Efficacy

Figure 5A:
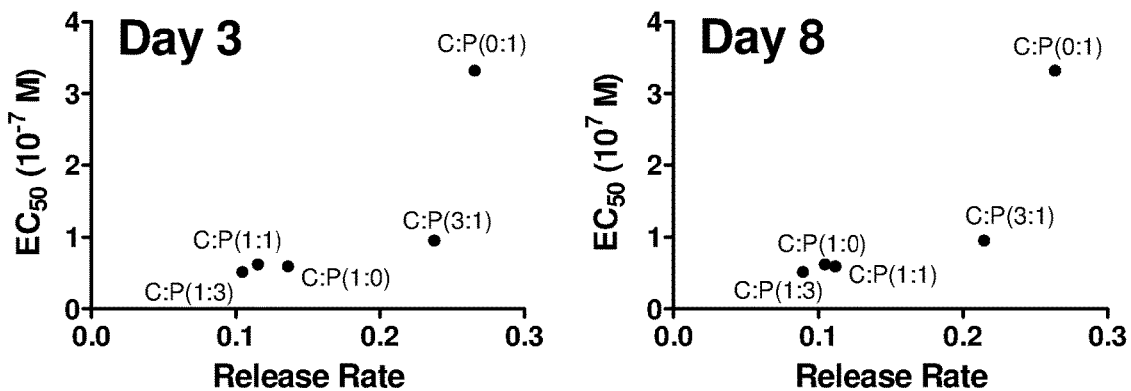
FIGS. 5A and 5B show the efficacy of liposomal BI 2536 is adjusted by tuning the citrate:phosphate ratio.
Figure 5B:
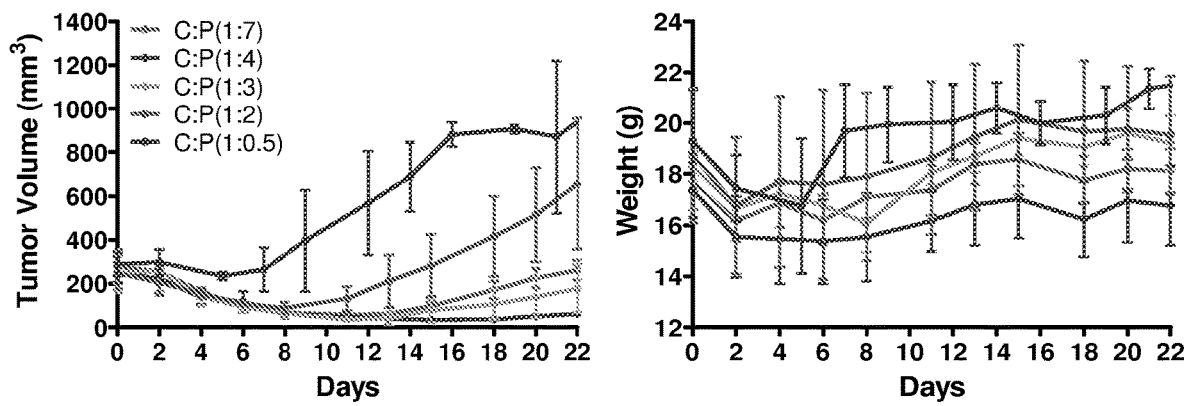

Since the two anions with the slowest release rates were citrate alone and the combination of citrate and phosphate (FIG. 4), varying the citrate:phosphate ratio was investigated to determine if it would have a substantial effect on efficacy. Formulations covering the ratios 0:1, 1:3, 1:1, 3:1 and 1:0 were tested in the same way as before for release rates and $EC_{50}$. The same trend with release rates and $EC_{50}$ was consistently observed, regardless of whether these variables were measured on days 3 or 8 of the cell cytotoxicity assay (FIG. 5A). Interestingly, it was noted that the slowest release was achieved with a citrate:phosphate ratio of 1:3, showing that this combinatorial ratio was synergistic and not just the averaged result of citrate alone and phosphate alone. This result further suggested that it was important to identify the optimal citrate:phosphate ratio in order to maximize in vivo efficacy in actual solid tumors. To identify this ratio, mice with established human colorectal cancer xenografts were treated with liposomes covering the citrate:phosphate ratios 1:7, 1:4, 1:3, 1:2 and 1:0.5. Consistent with the 1:3 ratio previously observed, the best in vivo efficacies were observed with citrate:phosphate ratios of 1:3 and 1:4 (FIG. 5B). Importantly, the decrease in tumor volumes for these ratios persisted over two weeks, an observation which is congruent with the expected slow release from these hyperstable liposomes. Although the 1:4 ratio produced an anti-tumor effect greater than 1:3, it also resulted in greater weight loss. Hence, 1:3 was adopted as the optimal ratio for subsequent experiments. BI 2536 encapsulated in this manner is referred to as "hyperstable."

Example 4

Hyperstable Liposomal BI 2536 Engenders Complete Responses in Mice

Figure 6A:
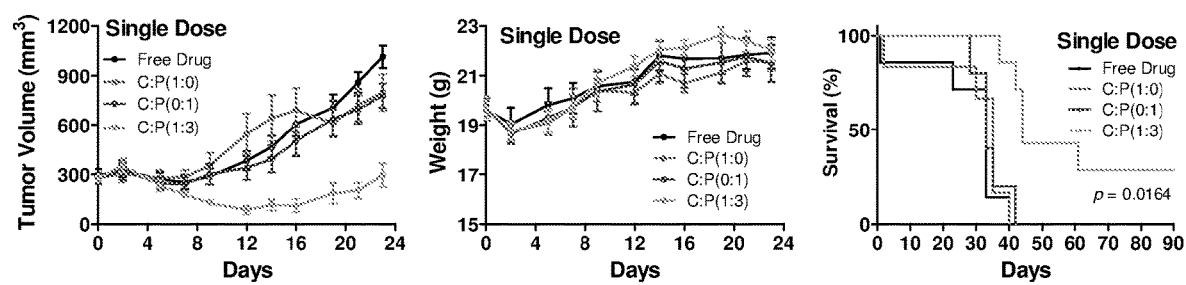
FIGS. 6A and 6B show in vivo efficacy and toxicity of liposomal BI 2536 on HCT116 xenografted mice. Tumor volumes and weights and Kaplan-Meier survival curves are shown for treatment with a single dose at day 0 (FIG. 6A) or double dose at days 0 and 7 (FIG. 6B). All treatments with liposomal BI 2536 were formulated with various citrate:phosphate (C:P) ratios as stated and administered at 340 mg/kg after accounting for encapsulation efficiency. Free BI 2536 was administered at the maximum tolerated dose of 100 mg/kg. Error bars represent standard errors. Tumor volumes are significantly different (p<0.05) between hyperstable liposomes (C:P=1:3)) and other groups from day 9 onwards for single dose and day 14 for double dose treatment. Mice treated with C:P(1:3) survived significantly longer (p<0.05) than other groups. Kaplan-Meier curve showing percentage survival over time. Ticks represent death events. The differences between BI-L2C6P and all other treatment were significant, Mantel-Cox Log-rank p-values are reported for the survival curves, showing that mice treated with C:P(1:3) survived significantly longer for both single (p=0.0164) and double (p=0.0349) dose treatments.

Nude mice bearing HCT116 xenografted tumors were treated with a single intravenous injection of hyperstable liposomal BI 2536, or liposomal BI 2536 with either only citrate or phosphate as an anion. Free unencapsulated BI 2536 was used as a control. Xenografts treated with hyperstable liposomes decreased in volume over 12 days, recapitulating the prolonged therapeutic effect observed in our previous animal experiment (FIG. 6A). In comparison, liposomes using only citrate or phosphate alone were indistinguishable from free drug, demonstrating that the combination of anions produces a synergistic effect not accounted for by either anion alone. Mice treated with hyperstable BI 2536 tended to have higher post-treatment weights, a trend which is consistent with the lower toxicity that one would expect with prolongation of drug release. Importantly, hyperstable BI 2536 significantly improved mouse survival with complete responses observed in two out of ten mice (Table 1). No complete responses were observed in the other experimental arms.

TABLE 1

Tabulation of Complete Responses for Various Treatments

| Treatment | Complete Responses | |
|---|---|---|
| | Single Dose | Double Dose |
| Free Drug | 0/10 | 0/8 |
| C:P (1:0) | 0/10 | 1/8 |
| C:P (0:1) | 0/10 | 0/10 |
| C:P (1:3) | 2/10 | 6/8 |

Figure 6B:
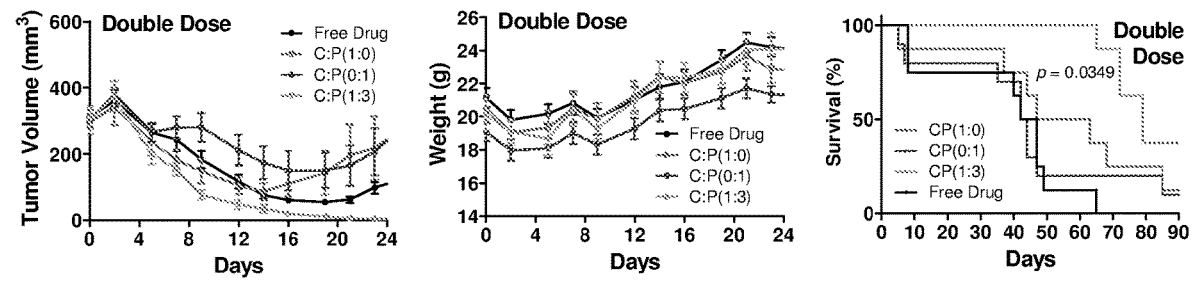

When the same experiment was repeated with two treatment doses 7 days apart instead of a single dose of hyperstable liposomes, the therapeutic effect was extended for an even longer period (FIG. 6B) and produced complete responses in 75% of the mice (Table 1). In contrast, no complete responses were observed in the other experimental arms. Hyperstable liposomes were not only more efficacious, but also well tolerated whereas all other experimental arms exhibited post-treatment toxicity.

Example 5

Hyperstable Liposomes Prolong the Tumor Presence and Efficacy of BI 2536

Figure 7A:
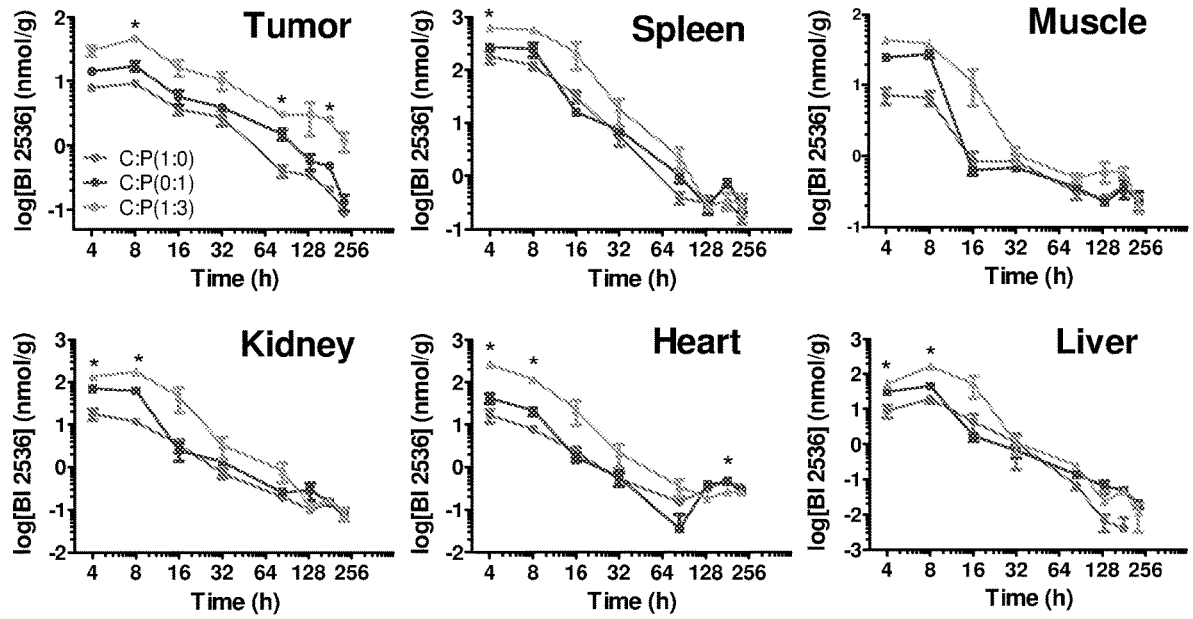
FIGS. 7A-7D show pharmacokinetics distribution and bioavailability of BI 2536 after treatment with hyperstable liposomal BI 2536.
Figure 7B:
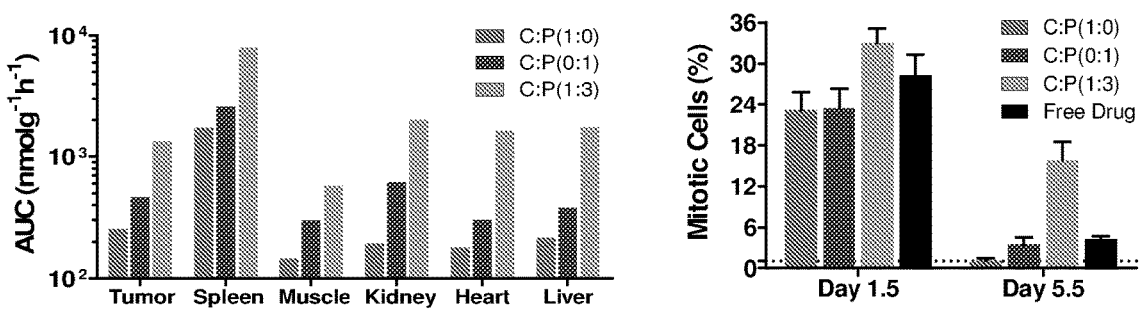
Figure 7C:
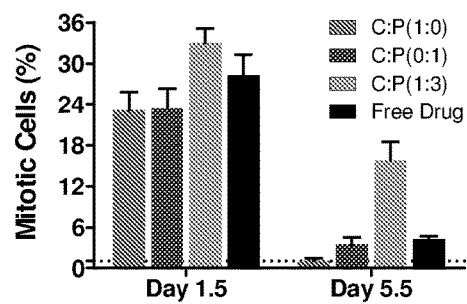
Figure 7D:
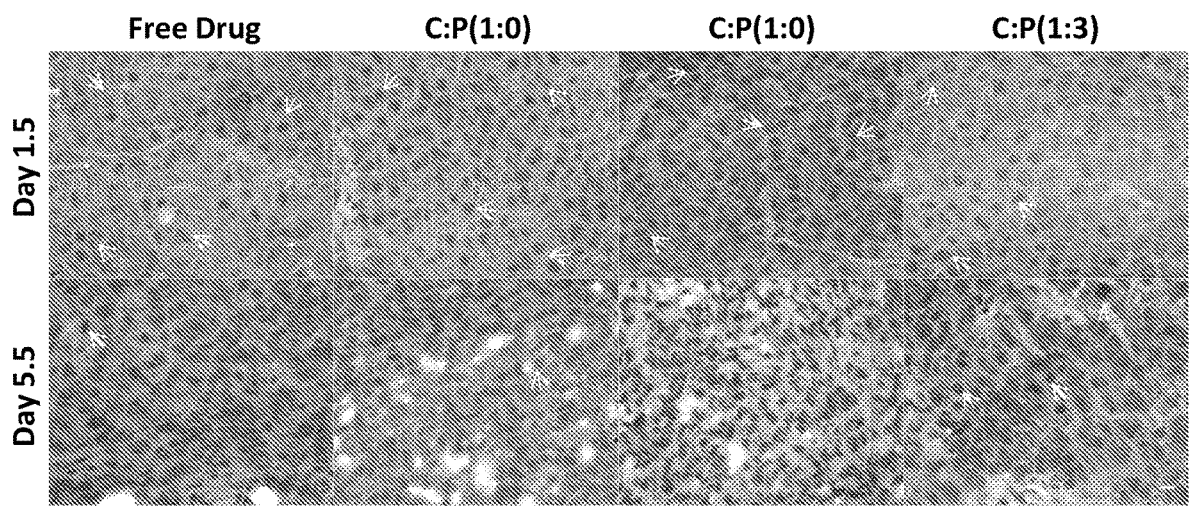

A reasonable explanation for the improved efficacy observed with hyperstable liposomes is that drug half-life is improved compared to regular PEGylated liposomes. Nude mice treated with a single dose of hyperstable liposomes showed significantly higher tumor concentrations of BI 2536 relative to control liposomes containing either citrate or phosphate alone (FIG. 7A; Table 2). This trend persisted over the entire 9.5 day period of measurement after which decreased tumor volumes made tissue processing impractical. Tumor exposure to hyperstable liposomal BI 2536 (as measured by the Area Under the Curve) was 5 times higher compared to citrate liposomes and 3 times higher compared to phosphate liposomes. Drug concentrations in healthy tissue (spleen, muscle, kidney, heart and liver) were similarly elevated for hyperstable liposomes although this trend was not statistically significant after 10 hours (FIG. 7A; Table 2). Despite these higher tissue concentrations, hyperstable liposomes were less toxic than control liposomes, suggesting that the majority of BI 2536 in a hyperstable liposome remains safely encapsulated while circulating through healthy tissue. Taken together with the general increase in Area Under the Curve, the data suggest that hyperstable encapsulation increases the circulating half-life of BI 2536, enhancing, as a result, the perfusion and retention of BI 2536 within the tumor compartment (FIG. 7B). The hallmark of BI 2536 (or any antimitotic chemotherapy) lies in its ability to inhibit mitotic division in tumors. To examine the question of whether higher bioavailability of BI 2536 could account for the difference between hyperstable liposomes and controls, histological analyses of the tumor samples on xenografts 1.5 and 5.5 days after a single dose of treatment was performed (FIGS. 7C and 7D). On day 1.5, all liposomal formulations of BI 2536 and encapsulated free BI 2536 were associated with mitotic figures being observed in approximately 25% of tumor nuclei in histological sections. However, by day 5.5, hyperstable liposomal BI 2536 was associated with a significantly higher proportion of mitotically-arrested cells in comparison to control liposomes and free drug. This extended temporal bioavailability is believed to accounts for the improved efficacy of hyperstably encapsulated BI 2536.

TABLE 2 p-values (2-tailed unequal variance t-test) comparing tissue concentrations of BI 2536 resulting from treatment with hyperstable liposomes (C:P = 1:3) versus other treatments (C:P = 1:0 and C:P = 0:1)

| | p values (2-tailed test, unequal variance) w.r.t. Lip_C:P(1:3) treatment | | | | | | | | | | | |
|---|---|---|---|---|---|---|---|---|---|---|---|---|
| Time | Tumor | | Spleen | | Muscle | | Kidney | | Heart | | Liver | |
| (h) | C:P(1:0) | C:P(0:1) | C:P(1:0) | C:P(0:1) | C:P(1:0) | C:P(0:1) | C:P(0:1) | C:P(0:1) | C:P(1:0) | C:P(0:1) | C:P(1:0) | C:P(0:1) |
| 4 | 0.0457 | 0.0874 | 0.0034 | 0.0019 | 0.0148 | 0.0584 | 0.0016 | 0.0075 | 0.0309 | 0.0345 | 0.0043 | 0.0384 |
| 8 | 0.0173 | 0.0147 | 0.0308 | 0.0521 | 0.0036 | 0.0844 | 0.0009 | 0.0021 | 0.0236 | 0.0237 | 0.0320 | 0.0477 |
| 16 | 0.1075 | 0.1362 | 0.2486 | 0.2225 | 0.2282 | 0.2219 | 0.2510 | 0.2443 | 0.2611 | 0.2526 | 0.2780 | 0.2600 |
| 32 | 0.1401 | 0.1876 | 0.3107 | 0.3687 | 0.5529 | 0.2917 | 0.2772 | 0.3765 | 0.2992 | 0.3080 | 0.9983 | 0.5652 |
| 84 | 0.0028 | 0.0132 | 0.2116 | 0.3501 | 0.1480 | 0.2395 | 0.2550 | 0.2903 | 0.3188 | 0.1696 | 0.0565 | 0.1395 |
| 132 | 0.2336 | 0.2621 | 0.6901 | 0.9838 | 0.2165 | 0.1886 | 0.2886 | 0.3148 | 0.0878 | 0.0374 | 0.5497 | 0.3018 |
| 180 | 0.0179 | 0.0220 | 0.8185 | 0.0990 | 0.1551 | 0.1585 | 0.3312 | 0.4393 | 0.0053 | 0.0166 | 0.0455 | 0.8493 |
| 228 | 0.1084 | 0.1148 | 0.4010 | 0.8696 | 0.8303 | 0.8053 | 0.8389 | 0.8251 | 0.0651 | 0.7096 | 0.3052 | 0.4443 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Dumontet, C. & Jordan, M. A. Microtubule-binding agents: a dynamic field of cancer therapeutics. *Nat. Rev. Drug Discov.* 9, 790-803 (2010).
2. Jordan, M. A. & Wilson, L. Microtubules as a target for anticancer drugs. *Nat. Rev. Cancer* 4, 253-265 (2004).
3. Gascoigne, K. E. & Taylor, S. S. How do anti-mitotic drugs kill cancer cells? *J. Cell Sci.* 122, 2579-2585 (2009).
4. Steegmaier, M. et al. BI 2536, a Potent and Selective Inhibitor of Polo-like Kinase 1, Inhibits Tumor Growth In Vivo. *Curr. Biol.* 17, 316-322 (2007).
5. Strebhardt, K. & Ullrich, A. Targeting polo-like kinase 1 for cancer therapy. *Nat. Rev. Cancer* 6, 321-330 (2006).
6. Sarli, V. & Giannis, A. Targeting the kinesin spindle protein: basic principles and clinical implications. *Clin. Cancer Res.* 14, 7583-7587 (2008).
7. Jackson, J. R., Patrick, D. R., Dar, M. M. & Huang, P. S. Targeted anti-mitotic therapies: can we improve on tubulin agents? *Nat. Rev. Cancer* 7, 107-117 (2007).
8. Keen, N. & Taylor, S. Aurora-kinase inhibitors as anticancer agents. *Nat. Rev. Cancer* 4, 927-936 (2004).
9. Gautschi, O. et al. Aurora kinases as anticancer drug targets. *Clin. Cancer Res.* 14, 1639-1648 (2008).
10. Komlodi-Pasztor, E., Sackett, D. L. & Fojo, A. T. Inhibitors targeting mitosis: tales of how great drugs against a promising target were brought down by a flawed rationale. *Clin. Cancer Res.* 18, 51-63 (2012).
11. Komlodi-Pasztor, E., Sackett, D., Wilkerson, J. & Fojo, T. Mitosis is not a key target of microtubule agents in patient tumors. *Nat. Rev. Clin. Oncol.* 8, 244-250 (2011).
12. Maeda, H. Toward a full understanding of the EPR effect in primary and metastatic tumors as well as issues related to its heterogeneity. *Adv. Drug Deliv. Rev.* 91, 3-6 (2015).
13. Matsumura, Y. & Maeda, H. A new concept for macromolecular therapeutics in cancer chemotherapy: mechanism of tumoritropic accumulation of proteins and the antitumor agent smancs. *Cancer Res.* 46, 6387-6392 (1986).
14. Barenholz, Y. (chezy). Doxil®—The first FDA-approved nano-drug: Lessons learned. *J. Control. Release* 160, 117-134 (2012).
15. Papahadjopoulos, D. et al. Sterically stabilized liposomes: improvements in pharmacokinetics and antitumor therapeutic efficacy. *Proc. Natl. Acad. Sci. U.S.A* 88, 11460-11464 (1991).
16. Fritze, A., Hens, F., Kimpfler, A., Schubert, R. & Peschka-Süss, R. Remote loading of doxorubicin into liposomes driven by a transmembrane phosphate gradient. *Biochim. Biophys. Acta* 1758, 1633-1640 (2006).
17. Cern, A. et al. Quantitative structure—property relationship modeling of remote liposome loading of drugs. *J. Control. Release* 160, 147-157 (2012).
18. Cheong, I. et al. A bacterial protein enhances the release and efficacy of liposomal cancer drugs. *Science* 314, 1308-1311 (2006).

19. Raab, M. et al. Mitotic arrest and slippage induced by pharmacological inhibition of Polo-like kinase 1. *Mol. Oncol.* 9, 140-154 (2015).
20. Dua, J. S. et. Liposome: methods of preparation and applications. Int'l J Pharmaceut Studies Res III (II):14-20 (2012).
21. Laouini, A et al. Preparation, characterization and applications of liposomes: state of the art. *J Colloid Sci Biotechnol* 1:147-168 (2012).
22. Budman, D. B. et at. (editors). *Handbook of Anticancer Drug Development*, Lippincott Williams & Wilkins (2003).
23. Saito, R. et al. Distribution of Liposomes into Brain and Rat Brain Tumor Models by Convection-Enhanced Delivery Monitored with Magnetic Resonance Imaging Cancer Research 64:2572-2579 (2004).
24. Mamot, C. et al. Extensive distribution of liposomes in rodent brains and brain tumors following convection-enhanced delivery. *J Neuro-Oncology* 68:1-9 (2004).
25. Gregoriadis, G. (editor), *Liposome Technology*, vol. 1-3, 1st edition, 1983; 2nd edition, 1993, CRC Press, Boca Raton, Fla.

What is claimed is:

1. A liposome that is hyperstable to release of an entrapped anti-mitotic drug from the liposome, the liposome comprising an inner milieu separated from an external environment by a membrane,
   A) wherein the inner milieu entraps:
      i) an anti-mitotic drug that is a polo-like kinase inhibitor, a kinase spindle inhibitor, or an aurora kinase inhibitor;
      ii) two anions selected from: citrate and phosphate; citrate and acetate; and acetate and phosphate, wherein the two anions are entrapped in the inner milieu in a molar ratio of about 1:3 or about 1:4; and
      iii) one or more cations,
   B) wherein the membrane comprises:
      i) 5% (mol/mol) 1,2-distearoyl-sn-glycerol-3-phosphoethanolamine-N-[methoxy (polyethylene glycol)-2000] (DSPE-PEG2000);
      ii) hydrogenated egg L-α-phosphatidyl-choline (HEPC); and
      iii) cholesterol (Chol), wherein the molar ratio of HEPC:Chol is 50:45,
   and
   wherein the liposome has a slow release physical property of less than 0.6% in 12 hours or less than 5% in 8 days release of the entrapped anti-mitotic drug from the liposome when suspended and incubated in vitro in 600 mM sucrose at 37° C.

2. The liposome of claim 1, wherein the two anions are present in a molar ratio of about 1:3.

3. The liposome of claim 1, wherein the two anions are citrate and phosphate or citrate and acetate.

4. The liposome of claim 1, wherein the one or more cations are sodium, ammonium, triethylammonium, copper, magnesium, zinc or iron.

5. The liposome of claim 1, wherein the polo-like kinase inhibitor is BI 2536 (4-[[(7R)-8-cyclopentyl-7-ethyl-5-methyl-6-oxo-7H-pteridin-2-yl]amino]-3-methoxy-N-(1-methylpiperidin-4-yl)benzamide), ON01910 (N-[2-methoxy-5-[[[2-(2,4,6-trimethoxyphenyl)-ethenyl]sulfonyl]methyl]phenyl]-glycine), GSK 461364 (5-[6-[(4-methyl-1-piperazinyl)methyl]-1-benzimidazolyl]-3-[(1R)-1-[2-(trifluoromethyl)phenyl]ethoxy]-2-thiophenecarboxamide), HMN 214 (N-(4-methoxyphenyl)sulfonyl-N-[2-[2-(1-oxido-4-pyridin-1-iumyl)ethenyl]phenyl]-acetamide) or BI 6727 (N-[4-[4-(cyclopropylmethyl)piperazin-1-yl]cyclohexyl]-4-[[(7R)-7-ethyl-5-methyl-6-oxo-8-propan-2-yl-7H-pteridin-2-yl]amino]-3-methoxybenzamide).

6. The liposome of claim 1, wherein the anti-mitotic drug is BI 2536 (4-[[(7R)-8-cyclopentyl-7-ethyl-5-methyl-6-oxo-7H-pteridin-2-yl]amino]-3-methoxy-N-(1-methyl-piperidin-4-yl)benzamide) or Ispinesib (N-(3-aminopropyl)-N-[(1R)-1-[7-chloro-4-oxo-3-(phenylmethyl)-2-quinazolinyl]-2-methylpropyl]-4-methylbenzamide).

7. A liposome composition comprising the liposome of claim 1 in an aqueous medium.

8. A pharmaceutical composition comprising the liposome of claim 1.

9. The pharmaceutical composition of claim 8, wherein the composition further comprises at least one pharmaceutically acceptable excipient and/or carrier.

10. The liposome of claim 1, wherein the kinesin spindle inhibitor is Ispinesib (SB 715992; N-(3-aminopropyl)-N-[(1R)-1-[7-chloro-4-oxo-3-(phenylmethyl)-2-quinazolinyl]-2-methylpropyl]-4-methylbenzamide), SB 743921 (N-(3-aminopropyl)-N-[(1R)-1-(3-benzyl-7-chloro-4-oxochromen-2-yl)-2-methylpropyl]-4-methylbenzamide), MK 0731 ((5S)-3-(2,5-difluorophenyl)-N-[(3R,4S)-3-fluoro-1-methylpiperidin-4-yl]-5-(hydroxymethyl)-N-methyl-5-phenyl-2H-pyrrole-1-carboxamide) or ARRY 520 ((2S)-2-(3-aminopropyl)-5-(2,5-difluorophenyl)-N-methoxy-N-methyl-2-phenyl-1,3,4-thiadiazole-3-carboxamide).

11. The liposome of claim 1, wherein the aurora kinase inhibitor is MK 0457 (VX 680; N-[4-[4-(4-methylpiperazin-1-yl)-6-[(5-methyl-1H-pyrazol-3-yl)amino]-pyrimidin-2-yl]sulfanylphenyl]cyclopropanecarboxamide), AZD 1152 (2-[ethyl-[3-[4-[[5-[2-(3-fluoroanilino)-2-oxoethyl]-1H-pyrazol-3-yl]amino]quinazolin-7-yl]oxypropyl]amino]ethyl dihydrogen phosphate), PHA 680632 (N-(2,6-diethylphenyl)-3-[[4-(4-methylpiperazin-1-yl)benzoyl]amino]-4,6-dihydro-1H-pyrrolo[3,4-c]pyrazole-5-carboxamide), PHA 739358 (N-[5-[(2R)-2-methoxy-1-oxo-2-phenylethyl]-4,6-dihydro-1H-pyrrolo[3,4-c]pyrazol-3-yl]-4-(4-methyl-1-piperazinyl)benzamide), MLN8054 (4-[[9-chloro-7-(2,6-difluorophenyl)-5H-pyrimido[5,4-d][2]benzazepin-2-yl]amino]benzoic acid), MLN8237 (4-[[9-chloro-7-(2-fluoro-6-methoxyphenyl)-5H-pyrimido[5,4-d][2]benzazepin-2-yl]amino]-2-methoxybenzoic acid), R763 ((1S,2S,3R,4R)-3-[[5-fluoro-2-[3-methyl-4-(4-methylpiperazin-1-yl)anilino]pyrimidin-4-yl]amino]bicyclo[2.2.1]hept-5-ene-2-carboxamide), AT9283 (1-cyclopropyl-3-[5-[6-(morpholin-4-ylmethyl)-1H-benzimidazol-2-yl]-1H-pyrazol-4-yl]urea), SNS 314 (1-(3-chlorophenyl)-3-[5-[2-(thieno[3,2-d]pyrimidin-4-ylamino)ethyl]-1,3-thiazol-2-yl]urea), SU 6668 (3-[2,4-dimethyl-5-[(Z)-(2-oxo-1H-indol-3-ylidene)methyl]-1H-pyrrol-3-yl]propanoic acid), ENMD 2076 ((2S,3S)-2,3-dihydroxybutanedioic acid; 6-(4-methylpiperazin-1-yl)-N-(5-methyl-1H-pyrazol-3-yl)-2-[(E)-2-phenylethenyl]pyrimidin-4-amine tartrate), CYC 116 (4-methyl-5-[2-(4-morpholin-4-ylanilino)pyrimidin-4-yl]-1,3-thiazol-2-amine), or ENMD 981693 (MKC 1693; (2S,3S)-2,3-dihydroxybutanedioic acid; 6-(4-methylpiperazin-1-yl)-N-(5-methyl-1H-pyrazol-3-yl)-2-[(E)-2-phenylethenyl]pyrimidin-4-amine).

12. The liposome of claim 1, wherein the two anions are present in a molar ratio of 1:4.

13. The liposome of claim 2, wherein the two anions are citrate and phosphate.

14. The liposome of claim 2, wherein the anti-mitotic drug is BI 2536 (4-[[(7R)-8-cyclopentyl-7-ethyl-5-methyl-6-oxo-7H-pteridin-2-yl]amino]-3-methoxy-N-(1-methyl-piperidin-4-yl)benzamide) or Ispinesib (N-(3-aminopropyl)-N-[(1R)-1-[7-chloro-4-oxo-3-(phenylmethyl)-2-quinazolinyl]-2-methylpropyl]-4-methylbenzamide).

15. The liposome of claim 12, wherein the anti-mitotic drug is BI 2536 (4-[[(7R)-8-cyclopentyl-7-ethyl-5-methyl-6-oxo-7H-pteridin-2-yl]amino]-3-methoxy-N-(1-methyl-piperidin-4-yl)benzamide) or Ispinesib (N-(3-aminopropyl)-N-[(1R)-1-[7-chloro-4-oxo-3-(phenylmethyl)-2-quinazolinyl]-2-methylpropyl]-4-methylbenzamide).

16. The liposome of claim 13, wherein the anti-mitotic drug is BI 2536 (4-[[(7R)-8-cyclopentyl-7-ethyl-5-methyl-6-oxo-7H-pteridin-2-yl]amino]-3-methoxy-N-(1-methylpiperidin-4-yl)benzamide) or Ispinesib (N-(3-aminopropyl)-N-[(1R)-1-[7-chloro-4-oxo-3-(phenylmethyl)-2-quinazolinyl]-2-methylpropyl]-4-methylbenzamide).

17. The liposome of claim 3, wherein the anti-mitotic drug is BI 2536 (4-[[(7R)-8-cyclopentyl-7-ethyl-5-methyl-6-oxo-7H-pteridin-2-yl]amino]-3-methoxy-N-(1-methylpiperidin-4-yl)benzamide) or Ispinesib (N-(3-aminopropyl)-N-[(1R)-1-[7-chloro-4-oxo-3-(phenylmethyl)-2-quinazolinyl]-2-methylpropyl]-4-methylbenzamide).

18. The liposome of claim 12, wherein the two anions are citrate and phosphate.

19. The liposome of claim 18, wherein the anti-mitotic drug is BI 2536 (4-[[(7R)-8-cyclopentyl-7-ethyl-5-methyl-6-oxo-7H-pteridin-2-yl]amino]-3-methoxy-N-(1-methylpiperidin-4-yl)benzamide) Ispinesib (N-(3-aminopropyl)-N-[(1R)-1-[7-chloro-4-oxo-3-(phenylmethyl)-2-quinazolinyl]-2-methylpropyl]-4-methylbenzamide).

20. A liposome that is hyperstable to release of an entrapped anti-mitotic drug from the liposome, the liposome comprising an inner milieu separated from an external environment by a membrane,
A) wherein the inner milieu entraps:
   i) comprising an anti-mitotic drug that is BI 2536 (4-[[(7R)-8-cyclopentyl-7-ethyl-5-methyl-6-oxo-7H-pteridin-2-yl]amino]-3-methoxy-N-(1-methyl-piperidin-4-yl)benzamide) or Ispinesib (N-(3-aminopropyl)-N-[(1R)-1-[7-chloro-4-oxo-3-(phenylmethyl)-2-quinazolinyl]-2-methylpropyl]-4-methylbenzamide);
   ii) citrate and phosphate in a molar ratio of about 1:3 or about 1:4;
   and
   iii) one or more cations,
B) wherein the membrane comprises:
   i) 5% (mol/mol) I,2-distearoyl-sn-glycerol-3-phosphoethanolamine-N-[methoxy (polyethylene glycol)-2000] (DSPE-PEG2000);
   ii) hydrogenated egg L-α-phosphatidyl-choline (HEPC); and
   iii) cholesterol (Chol), wherein the molar ratio of HEPC:Chol is 50:45,
and
wherein the liposome has a slow release physical property of less than 0.6% in 12 hours or less than 5% in 8 days release of the entrapped anti-mitotic drug from the liposome when suspended and incubated in vitro in 600 mM sucrose at 37° C.

* * * * *

UNITED STATES PATENT AND TRADEMARK OFFICE
CERTIFICATE OF CORRECTION

PATENT NO. : 11,331,272 B2
APPLICATION NO. : 16/478278
DATED : May 17, 2022
INVENTOR(S) : Chang Zhi Adrian Ng et al.

It is certified that error appears in the above-identified patent and that said Letters Patent is hereby corrected as shown below:

In the Claims

In Column 19, Line 30, in Claim 1, delete "kinase spindle" and insert --kinesin spindle--.

In Column 21, Line 28, in Claim 19, after "benzamide)" insert --or--.

Signed and Sealed this
Seventeenth Day of September, 2024

Katherine Kelly Vidal
*Director of the United States Patent and Trademark Office*